(12) United States Patent
Al-Lamee

(10) Patent No.: US 6,756,125 B2
(45) Date of Patent: Jun. 29, 2004

(54) BIOCOMPATIBLE MEDICAL ARTICLES AND PROCESS FOR THEIR PRODUCTION

(75) Inventor: Kadam Gayad Al-Lamee, Yorkshire (GB)

(73) Assignee: Polybiomed Limited, Sheffield (GB)

( * ) Notice: Subject to any disclaimer, the term of this patent is extended or adjusted under 35 U.S.C. 154(b) by 0 days.

(21) Appl. No.: 10/148,709

(22) PCT Filed: Nov. 29, 2000

(86) PCT No.: PCT/GB00/04538

§ 371 (c)(1),
(2), (4) Date: Sep. 23, 2002

(87) PCT Pub. No.: WO01/39814

PCT Pub. Date: Jun. 7, 2001

(65) Prior Publication Data

US 2003/0059631 A1 Mar. 27, 2003

(30) Foreign Application Priority Data

Nov. 29, 1999 (GB) ............................................. 9928071

(51) Int. Cl.$^7$ ................................................. B23B 9/04
(52) U.S. Cl. ............................ 428/447; 528/38; 536/21
(58) Field of Search ........................... 428/447; 528/38; 536/21

(56) References Cited

U.S. PATENT DOCUMENTS

| | | | |
|---|---|---|---|
| 4,678,468 A | 7/1987 | Hiroyoshi | 623/1 |
| 5,182,317 A | 1/1993 | Winters et al. | 523/112 |
| 5,541,167 A | 7/1996 | Hsu et al. | 514/56 |
| 5,541,305 A * | 7/1996 | Yokota et al. | 536/21 |
| 6,119,028 A * | 9/2000 | Schulman et al. | 600/345 |

FOREIGN PATENT DOCUMENTS

| | | |
|---|---|---|
| EP | 0338418 | 10/1989 |
| EP | 0941740 | 9/1999 |
| GB | 1136669 | 12/1968 |

* cited by examiner

*Primary Examiner*—Margaret G. Moore
(74) *Attorney, Agent, or Firm*—Nixon & Vanderhye

(57) ABSTRACT

An article of metal, glass, ceramics or plastics having a surface for contact with tissue or with circulating blood, has a surface coating of an organopolysiloxane and heparin, in which coating the organopolysiloxane is adherent to the surface of the article and has cationic groups that form ionic bonds with anionic groups of the heparin. The surface for contact with circulating blood may be an interior surface of a cannula or tubing or of a blood oxygenator or it may be a working surface of a blood filter. The polymer may be poly-[dimethylsiloxane-co-methyl-(3-hydroxypropyl)siloxane]-graft-poly(ethylene glycol) [3-(trimethylammonio) propyl chloride] ether. A method is also provided for forming a coated article as aforesaid, said method comprising contacting said surface with a solution in a volatile organic solvent of an organopolysiloxane and with heparin, the organopolysiloxane being adherent to the surface of the article and having cationic groups that form ionic bonds with the anionic groups of the heparin, and removing said volatile solvent.

21 Claims, No Drawings

BIOCOMPATIBLE MEDICAL ARTICLES AND PROCESS FOR THEIR PRODUCTION

CROSS-REFERENCE TO RELATED APPLICATIONS

This application is a national phase application of International Application No. PCT/GB00/04538, which was filed on Nov. 29, 2000 and which published in English on Jun. 7, 2001, which in turn claims priority from Application No. GB 9928071.1, which was filed on Nov. 29, 1999.

FIELD OF THE INVENTION

This invention relates to medical articles that can be placed in contact with a stream of blood or other tissue and which have surfaces that are anti-thrombogenic. It also relates to a process for treating a medical article to impart anti-thrombogenic properties to a surface thereof.

BACKGROUND TO THE INVENTION

Articles for contact with circulating blood, whether intracorporeally or during extracorporeal blood circulation, can give rise to coagulation. In particular, plastics materials have been found to be thrombogenic, even in the case of relatively blood-compatible materials such as polytetrafluoroethylene and silicone rubber. In order to minimize trauma in blood circulating in contact with articles having non-biological surfaces, bonding of heparin to such surfaces has been disclosed, the heparin imparting anti-thrombogenic properties.

Bonding of heparin to surfaces was first described by V. I. Gott et. Al., Science, 142, 1297 (1963), the surfaces being graphitized, treated with benzalkonium chloride and then with heparin. Subsequently a simpler surface treatment was developed based on coating the surface e.g. by simple immersion with a thin layer of tridodecylmethyl ammonium heparinate, see V. I. Gott et. al., Ann. Thoracic Surg., 14, 219 (1972) and A. H. Krause et. al, Ann. Thoracic Surg., 14, 123 (1972). According to a data sheet issued by Polysciences Limited of Northampton, England in 1984 the process was used to make shunts for use in artery bypass. Greater stability to washing can be achieved by cross-linking the bonded heparin molecules with dialdehydes, see U.S. Pat. No. 3,810,781 (Eriksson), and an increased level of heparin uptake can be achieved in the case of plastics articles by glow-or corona-treating the surface of the article, see U.S. Pat. No. 4,613,517. The use of so-called "Duraflo II heparin" coatings to reduce blood trauma in extracorporeal circuits e.g. of cardiopulmonary bypass machines is disclosed by Li-Chien Hsu, Cardiac Surgery: state of the art reviews-Vol. 7, No. 2, 265 (1993). The effectiveness of so-called "heparin bonded circuits" in reducing the need for blood transfusion during coronary artery bypass surgery is disclosed by G. M. Mahoney et. al., European Journal of Cardio-thoracic Surgery.

Various references disclose the treatment of surfaces with heparin and with a silicone. For example U.S. Pat. No. 4,529,614 (Burns) discloses the coating of microcontainer tubes for use in blood testing with an aqueous solution of heparin and an organopolysiloxane to form a hydrophobic anticoagulant layer. U.S. Pat. No. 5,061,738 (Solomon et al) discloses a medical device such as a probe, cannula or catheter which is rendered both antithrombogenic and lubricious by treatment of a mixture of a quaternary ammonium complex of heparin and a non-curing lubricating silicone which may be a polydialkylsiloxane. U.S. Pat. No. 5,182,317 (Winters et. al.) discloses the production of multi-functional thrombo-resistant coatings for use with biomedical devices and implants. A material is prepared which has a siloxane surface onto which a plurality of amine functional groups is bonded. Either the surface is plasma etched with ammonia gas or a siloxane monomer is plasma polymerized in the presence of ammonia gas. The resulting siloxane surface containing amine groups is reacted with poly (ethylene oxide) chains terminated with functional groups that can react with the amine groups on the siloxane surface. The product is then further reacted with at least two different molecules that are capable of resisting blood material incompatibility reactions. U.S. Pat. No. 5,541,167 discloses a device for removing air bubbles from blood ("defoaming") before the blood is returned to a patient. Sequential coatings of a quaternary ammonium complex of heparin and of a mixture of a polysiloxane and silicon dioxide are applied.

SUMMARY OF THE INVENTION

The present invention provides a polymeric coating that may be applied to an article for surgery, diagnosis or other medical treatment and in which heparin and/or or another negatively charged biologically active molecule is simply and effectively bound to a substrate.

The substrate is treated with a polydimethylsiloxane-based primer which adheres firmly to the surface of the article without the need for pre-treatment (e.g. by plasma discharge or by a coupling agent) and which has exposed cationic sites. The primer forms a thin transparent layer and is not detrimental to the mechanical properties of the device. Simultaneously or subsequently the heparin and/or other negatively charged biologically active molecules are applied to the article. Treatment can be carried out at ambient temperatures. After treatment the article may be washed to remove solvent and un-reacted reagent and dried either with moderate heat insufficient for reduction of the biological activity of the heparin to take place or at ambient temperatures.

In one aspect the invention provides an article having a surface for contact with circulating blood, said surface having a coating of an organopolysiloxane and heparin, wherein the organopolysiloxane is adherent to the surface of the article and has cationic groups that form ionic bonds with anionic groups of the heparin.

In another aspect the invention provides an article having a surface for contact with circulating blood, said surface having a coating of an organopolysiloxane and a biologically active material having anionic groups, wherein the organopolysiloxane is adherent to the surface of the article and has cationic groups that form ionic bonds with anionic groups of the biologically active material. The anionic biologically active molecule may, for example be a diagnostic agent, growth factor, antibody. prostaglandin (which can inhibit thrombus formation and platelet activity) or protein.

In a further aspect, the invention provides a method for forming a coated article as defined above, said method comprising:

contacting said surface with a solution in a volatile organic solvent of an organopolysiloxane and with heparin, the organopolysiloxane being adherent to the surface of the article and having cationic groups that form ionic bonds with the anionic groups of the heparin; and removing said volatile solvent.

The surface of the article may be coated sequentially with the organopolysiloxane and with heparin, or a complex of the organopolysiloxane and heparin may be formed in solution, after which the solution is contacted with the surface of the article. The process may be applied to the coating of other negatively charged biologically active molecules in addition to or as an alternative to coating with heparin.

Use of the article in the recirculation of blood e.g. as a blood line, oxygenator, heat exchanger, haemodyalyser and/or blood filter is also within the scope of the invention. When heparin treated oxygenators or haemodyalysers are used, the dose of heparin that has to be administered to the patient to enable the treatment to be conducted safely can be reduced.

Description of Preferred Features

The article to be rendered bio-compatible may be at least partly of a metal, ceramics or glass. It may also be at least partly of a polymeric material, e.g. polyethylene, polyacrylic, polypropylene, polyvinyl chloride, polyamide, polyurethane, polyvinyl pyrrolidone, polyvinyl alcohol, polystyrene, polysulfone, polytetrafluoroethylene, polyester, silicone rubber, natural rubber, polycarbonate or a hydrogel. The invention is particularly advantageous for the treatment of hollow articles in which the surface for contact with circulating blood is an interior surface, e.g. a cannula or tubing, a blood oxygenator (which may be provided with a reservoir and heat exchanger) or blood filter or haemodyalyser.

The organopolysiloxane is preferably soluble in a lower alcohol, of which 2-propanol is preferred because of its combination of volatility and antiseptic properties. It preferably has trimethylammonium groups linked to a polydimethylsiloxane main chain by grafted polyoxyethylene chains, which preferably include hydroxyl terminated chains, and quaternary ammonium terminated chains. A particular preferred cationic solvent-soluble silicone polymer used is poly-[dimethylsiloxane-co-methyl-(3-hydroxypropyl) siloxane]-graft-poly(ethylene glycol) [3-(trimethylammonio) propyl chloride] ether whose structure is believed to be generally as indicated below:

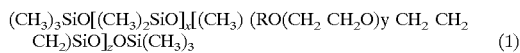

$(CH_3)_3SiO[(CH_3)_2SiO]_x[(CH_3)(RO(CH_2CH_2O)yCH_2CH_2CH_2)SiO]_zOSi(CH_3)_3$  (1)

wherein x, y and z represent integers and R, whose value may differ in different units along the chain, represents H or -[$CH_2CH_2CH_2N^+(CH_3)_3$] X wherein X represents chloride or another cation. The material used may typically have a molecular mass of about 4000 and about 4 quaternary ammonium groups per molecule.

The organopolysiloxane may be contacted with the surface of the article whilst it is in solution in an alcohol or aqueous alcohol e.g. 2-propanol. Contact may be at ambient temperatures, and in the case of a hollow article it can simply involve circulation of the solution through the article to permit the organopolysiloxane to form a layer on the surface to be treated. If the ionic complex is not preformed, the heparin or other biologically active material may be applied as an aqueous solution at ambient temperatures, so that the procedures involved are relatively rapid and inexpensive. In the case of an aqueous/alcohol mixture, the alcohol should predominate, a ratio of 1:10 helping to solubilize hydrophilic materials whilst preserving the antiseptic qualities of the alcohol. Where the surface to be treated is one face of a membrane or tube of microporous material (e.g. microporous polypropylene or polysulfone fibers), gas under pressure is preferably supplied to the other face of the membrane or tube to keep the pores open.

The process has been applied successfully to medical devices such as oxygenators, blood filters, and PVC tubing used in glucose monitoring systems, and the coated articles have been successfully tested for biocompatibility. The process has also been applied to haemodyalysers, and both the case and the fibrous membranes of a haemodyalyser have been successfully coated. Our experiment was carried out with a haemodyalyser having microporous polysulfone membranes and a polycarbonate case.

The invention will now be further described, by way of example only with reference to the following examples:

EXAMPLE I

Treatment of a Hollow Fiber Oxygenator

Experiments were carried out to determine conditions for the treatment of a hollow fiber blood oxygenator. Such an oxygenator is a single use device, which is used for oxygenating blood during cardiac surgery. Blood is diverted from the right atrium and pumped along tubing by means of a peristaltic pump into a reservoir, which gives the perfusionist a volume of blood on which to work. The blood is then directed from the reservoir to a heat exchanger compartment of the oxygenator, where it can be heated or cooled according to demand by water flowing through heat exchanger tubes of polyethylene or stainless steel. Blood proceeds from the heat exchanger into an oxygenator compartment where oxygen is introduced into the blood by contact with the surfaces of hollow fibrous tubes of microporous plastics material e.g. polypropylene. The use of fibers is not critical and other oxygenators use membranes e.g. of silicone. Blood is returned to the patient via the aorta. The use of a cardiopulmonary bypass circuit including a heat exchanger and oxygenator unit of the above kind allows the surgeon to cool the heart to reduce its oxygen demand and then stop the heart beating for a period of time while he is working on the heart. The use of such a by-pass also allows all the blood to be drained from the veins and arteries of the heart.

An object of the present experiment was to find a way of improving the biocompatibility of the internal surfaces of the reservoir, heat exchange compartment and oxygenator compartment and providing them with a surface layer which was non-thrombogenic.

A 1% solution of the polymer (I) in 2-propanol (from Sigma-Aldrich company Ltd, Poole, Dorset) was circulated through an oxygenator assembly as described above for a period of 15 minutes and at a rate of 0.7 liters/minute. Oxygen at a positive pressure of 0.1 atmosphere was supplied to the "$O_2$ in" line to prevent liquid entering the gas side of the oxygenator and to keep the pores of the hollow fibres open and so maintain the oxygen-permeability of the device. After the circulation step had been completed, excess 2-propanol solution was blown out of the oxygenator with gas from the oxygen line. The apparatus was then rinsed with de-ionized water, the de-ionized water was blown out using oxygen gas, and the apparatus was dried in an oven at 50° C. overnight. The various internal surfaces of the assembly were then tested with Eosin Y. A red stain developed at each surface, which was taken as an indication that the polymer (I) had become attached.

A second oxygenator assembly was treated as indicated above, after which a 0.1% solution of heparin (Celsus) in de-ionized water was circulated for about 5 hours, again with a positive pressure of oxygen in the "$O_2$ in" line. The oxygen line was then used to blow excess heparin solution out of the assembly. The apparatus was then again washed with de-ionized water, the de-ionized water was blown out using oxygen gas, and the assembly was oven-dried at 50° C. overnight. The internal surfaces of the assembly were contacted with toluidene blue. A dark purple stain developed on the fibers within the oxygenator, and also on the walls of the oxygenator which were of polycarbonate. This was taken as an indication that the heparin had become ionically bonded to the previously formed internal coating of polymer (I).

Blood (about 500 ml) from an abattoir was treated with a solution of heparin (0.2 g) in saline (0.9%; 50 ml) to allow it to be transported to the laboratory without coagulation. Protamine sulfate was added to the fully heparinized blood to reduce the ACT (activated clotting time) to about 200–400 sec which is comparable to that of untreated fresh blood. The following procedure was adopted to determine the amount of protamine sulfate to be added. A solution of protamine sulfate (0.1 g) was prepared. A sample of the blood was steadily agitated and 20 ml was introduced into a plastics container, followed by about 200 ] of the protamine sulfate solution. Two ml of the resulting solution were withdrawn and placed into a flip top tube of a Haemochron whole blood coagulation system. The tube was placed into a Haemochron 401 coagulation detector that measures the length of time that the blood takes to clot (ACT). The volumes of the protamine sulfate solution was varied as required to bring the measured ACT within the 200–400 sec range set out above. Then protamine sulfate was then added to the remainder of the 500 ml of fully heparinised blood in the ratio indicated by the preceding test.

The heparinised and protamine sulfate treated blood was then circulated through an oxygenator treated with the polymer (I) alone, and through an oxygenator treated with both the polymer (I) and with heparin. In the former case, the blood clotted immediately, whereas in the second case the measured ACT was above 1500 seconds which was much more that of the blood at the start of the experiment. This was taken to indicate that heparin was being released from the coated internal surface of the apparatus and was effective to inhibit clotting.

Oxygenators treated as described above were found to pass cytotoxicity and haemolysis tests by a wide margin.

EXAMPLE 2

A 0.1 wt % solution of polymer (I) in 2-propanol was circulated through an oxygenator assembly as described in Example 1 at 80 ml/minute for 30 minutes, during which time air from a compressor was supplied to the "$O_2$ in" line. Excess polymer (I) solution was then flushed out with oxygen, after which the oxygenator was dried at 50° C. for about 7 hours with air from the compressor being supplied to both the "$O_2$ in" line and the "blood in" line. De-ionized water was then circulated through the oxygenator at a rate of 80 ml/min for about 1 hour, during which time air from the compressor was supplied to the "$O_2$ in" line.

A 0.1 wt % solution of heparin in de-ionized water was then circulated through the oxygenator for about 1 hour at a rate of 80 ml/min, during which time air from the compressor was supplied to the "$O_2$ in" line. De-ionized water was then circulated through the oxygenator for about 1 hour at 80 ml/min while air from the compressor continued to be supplied to the "$O_2$ in" line. Oxygen was then blown through the oxygenator to flush out most of the de-ionized water, after which the oxygenator was dried at room temperature (to avoid thermal reduction of the heparin bioactivity) for 12.5 hours, with the compressor supplying air to the "$O_2$ in" line and to the "blood in" line. The oxygenator was then ready for use.

An oxygenator treated as indicated above was found to have a generally constant ACT over a blood circulation period of 7 hours and to be free from leakage of blood into the "$O_2$ in" line.

EXAMPLE 3

A solution of polymer (I) (0.88 g) in 2-propanol (350 g) was mixed with a solution of heparin (0.05 g) in de-ionized water (50 g). Mixing was continued for 15 minutes, after which the mixture was circulated through an oxygenator as described in the preceding examples for a period of 30 minutes, during which time air from the compressor was supplied to the "$O_2$ in" line. De-ionized water was then circulated through the oxygenator for about 1 hour at 80 ml/min while air from the compressor continued to be supplied to the "$O_2$ in" line. Oxygen was then blown through the oxygenator to flush out most of the de-ionized water, after which the oxygenator was dried at room temperature for 6 hours to avoid thermal degradation of the heparin, with the compressor supplying air to the "$O_2$ in" line and to the "blood in" line. The working surfaces of the oxygenator were tested with toluidine blue and a dark purple stain developed. This was taken as an indication that the heparin had become ionically bonded to the polymer (I) which had during the subsequent circulation step formed a coating on the working surfaces of the oxygenator.

EXAMPLE 4

Animal Trial

Several components of Extracorporeal products such as Safe Mini oxygenators, reservoirs and silicone tubes were coated with polymer (I) and then coupled with heparin using the method described in example 2.

The heparin coated oxygenators, reservoir and silicone tubes were then used for in-vivo test with a pig model and compared with uncoated circuit. The objective was to show the difference between heparin coated and uncoated product during in-vivo test of an Extracorporeal circulation (ECC) at a reduced ACT level over the time of the test due to the body metabolism of the animal. The tests were carried out in parallel using either two or four Safe Mini Oxygenators for each run. The design of this test is to make sure that the coated and uncoated products can be compared under identical conditions. The initial levels of ACT was approximately 480 seconds, which is normally recommended with ECC. After 2–3 hours of circulation, the ACT level was in the region of 125–200 seconds.

During this test the products were examined for the presence of any clotting and photographs were taken at the end of the test. All products were then flushed with saline and inspected for clotting or any other blood deposition.

Results:

(1) It was clearly observed that micro clots deposited on all six uncoated products especially when the ACT reached to 250 seconds. The amount and the size of the clot were also increased when the ACT was decreased further at the advancing time of the test.

(2) On the other hand no visible clots were seen onto the six heparin coated products.

(3) No significant increase in pressure drop was observed, except in the first pair of products, where the pressure drop increased 20 mmHg in total for the coated one and 72 mmHg for the uncoated products.

(4) Significant amounts of clots were observed onto the surface of the uncoated products after flushing the blood with slain.

(5) No signs of clots onto the surface of heparin coated products were shown after flushing the blood with slain. Few blood depositions were seen in some areas of these products which are insignificant compare to the uncoated products.

What is claimed is:

1. An article having a surface for contact with circulating blood, said surface having a coating of an organopolysiloxane and heparin, wherein the organopolysiloxane is soluble in an alcohol and wherein the organopolvsiloxane is adherent to the surface of the article and has cationic groups that form ionic bonds with anionic groups of the heparin.

2. The article of claim 1, wherein the article is at least partly made from a metal, ceramic or glass.

3. The article of claim 1, wherein the article is at least partly made from a polymeric material.

4. The article of claim 3, wherein the article is made from polyethylene, polyacrylic, polypropylene, polyvinyl chloride, polyamide, polyurethane, polyvinyl pyrrolidone, polyvinyl alcohol, polystyrene, polytetrafluoroethylene, polyester, silicone rubber, natural rubber, polycarbonate or a hydrogel.

5. The article of claim 1, wherein the article is hollow and the surface for contact with circulating blood is an interior surface.

6. The article of claim 1, wherein the article is a cannula or tubing.

7. The article of claim 1, wherein the article is a blood oxygenator, blood filter or haemodyalyser.

8. The article of claim 1, wherein the organopolysiloxane is adherent without a coupling agent.

9. The article of claim 1, wherein the organopolysiloxane has triethylammonium groups.

10. The article of claim 1, wherein the organopolysiloxane has cationic groups linked to a polydimethylsiloxane main chain by grafted polyoxyethylene chains.

11. The article of claim 10, wherein the grafted polyoxyethylene chains include hydroxyl terminated chains and quaternary ammonium terminated chains.

12. The article of claim 1, wherein the organopolysiloxane is poly[dimethylsiloxane-co-methyl-(3-hydroxypropyl)siloxane]graft-poly(ethyleneglycol) [3-(trimethylammonio) propyl chloride] ether.

13. A method for forming a coated article having a surface for contact with circulating blood, the surface having a coating of an organopolysiloxane and heparin, the method comprising:

(a) contacting the surface with a solution in a volatile organic solvent of the organopolysiloxane and with heparin, wherein the organopolysiloxane is adherent to the surface of the article and comprises cationic groups and heparin comprises anionic groups, wherein the cationic groups of the organopolysiloxane form ionic bonds with the anionic groups of the heparin; and (b) removing the volatile solvent.

14. The method of claim 13, wherein the surface of the article is coated sequentially with the organopolysiloxane and with heparin.

15. The method of claim 13, wherein a complex of organopolysiloxane and an alcohol is formed in solution and the solution is contacted with the surface of the article.

16. The method of claim 13, wherein the organopolysiloxane contacted with the surface of the article is in splution in an alcohol.

17. The method of claim 16, wherein the alcohol is 2-propanol.

18. The method of claim 13, wherein the surface to be treated is one face of a membrane or tube of microporous material and a gas under pressure is supplied to the other face of the membrane or tube.

19. An article having a surface for contact with circulating blood, said surface having a coating of an organopolysiloxane and a biologically active material having anionic groups, wherein the organopolysiloxane is soluble in an alcohol and wherein the organopolysiloxane is adherent to the surface of the article and has cationic groups that form ionic bonds with anionic groups of the biologically active material.

20. The article of claim 19, wherein the biologically active molecule is a diagnostic agent, growth factor, or antibody, prostaglandin or protein.

21. A method for forming a coated article having a surface for contact with circulating blood, the surface having a coating of an organopolysiloxane and heparin, the method comprising:

(a) contacting the surface with a solution in an alcohol of the organopolysiloxane to form a surface coated with the organopolysiloxane;

(b) removing the alcohol; and (c) contacting the surface coated with the organopolysiloxane with an aqueous solution of heparin, wherein the organopolysiloxane comprises cationic groups and the heparin comprises anionic groups, and the cationic groups of the organopolysiloxane form ionic bonds with the anionic groups of the heparin.

* * * * *